US006184415B1

(12) United States Patent
Samsel et al.

(10) Patent No.: US 6,184,415 B1
(45) Date of Patent: Feb. 6, 2001

(54) PRODUCTION OF CHIRAL NON-RACEMIC 2-HALOPROPIONIC ACID OR SALT THEREOF

(75) Inventors: Edward G. Samsel; Christi R. Bedell, both of Baton Rouge, LA (US)

(73) Assignee: Albemarle Corporation, Richmond, VA (US)

(*) Notice: Under 35 U.S.C. 154(b), the term of this patent shall be extended for 0 days.

(21) Appl. No.: 09/431,515

(22) Filed: Nov. 1, 1999

(51) Int. Cl.⁷ .................................................. C07C 53/15
(52) U.S. Cl. ............................................. 562/602; 562/605
(58) Field of Search ...................................... 562/602, 605

(56) References Cited

U.S. PATENT DOCUMENTS

| | | |
|---|---|---|
| 4,691,037 | 9/1987 | Yoshikawa et al. . |
| 4,766,220 | 8/1988 | Gras . |
| 4,766,225 | 8/1988 | Sayo et al. . |
| 4,962,230 | 10/1990 | Takaya et al. . |
| 4,994,590 | 2/1991 | Takaya et al. . |
| 4,994,607 | 2/1991 | Chan . |
| 5,144,050 | 9/1992 | Chan et al. . |
| 5,177,231 | 1/1993 | Manimaran et al. . |
| 5,187,135 | 2/1993 | Kolich et al. . |
| 5,187,136 | 2/1993 | Klobucar et al. . |
| 5,187,281 | 2/1993 | Kolich et al. . |
| 5,190,905 | 3/1993 | Kolich et al. . |
| 5,191,095 | 3/1993 | Manimaran et al. . |
| 5,198,561 | 3/1993 | Chan et al. . |
| 5,202,472 | 4/1993 | Manimaran et al. . |
| 5,202,473 | 4/1993 | Chan et al. . |
| 5,210,243 | 5/1993 | Kolich . |
| 5,304,524 | 4/1994 | Klobucar et al. . |
| 5,852,212 * | 12/1998 | Broger et al. . |

FOREIGN PATENT DOCUMENTS

| | | |
|---|---|---|
| 0245959 | 11/1987 | (EP) . |
| 0256634 | 2/1988 | (EP) . |
| 0272787 | 6/1988 | (EP) . |
| 0174057 | 8/1988 | (EP) . |
| 9830522 | 7/1998 | (WO) . |

OTHER PUBLICATIONS

Saburi et al, "Asymmetric Hydrogenation of 2–Fluoro–2–Alkenoic Acids Catalyzed by Ru–binap Complexes" Tet. Lett. vol. 33 No. 51 pp. 7877–7880, 1992.*
Comp. Org. Syn., vol. 8, Selectivity, Strategy, & efficiency in Modern Organic Chemistry, 1991, pp. 459–469.
Chan, A., et al., "Preparation and structural characterization of bis(acetylacetonato)ruthenium(II)–BINAP: an efficient route to an effective asymmetric hydrogenation catalyst precursor", Inorganica Chimica Acta, vol. 228, 1995, pp. 159–163.
Chan, A., et al., "An improved synthesis of Ru(BINAP) type complexes", Inorganica Chimica Acta, vol. 223, 1994, pp. 165–167.
Genet, J.P., et al., "General Synthesis of Novel Chiral Ruthenium Catalysts and Their Use in Asymmetric Hydrogenation", Tetrahedron: Asymmetry, vol. 2, No. 1, 1991, pp. 43–46.
Ikariya, T., et al., "Synthesis of Novel Chiral Ruthenium Complexes of 2,2'Bis(diphenylphosphino)–1,1'–binaphthyl and Their Use as Asymmetric Catalysts", J. Chem. Commun., 1985, pp. 922–924.
Mashima, K., et al., "Synthesis of New Cationic BINAP–Ruthenium(II) Complexes and Their Use in Asymmetric Hydrogenation [BINAP=2,2'–bis(di–phenylphosphino)–1,1'–binaphthyl]", J. Chem.. Soc., Chem. Commun., 1989, pp. 1208–1210.
Manimaran, T., et al., "In Situ Generation of Ruthenium–Chiral Phosphine Complexes and Their Use in Asymmetric Hydrogenation", Organometallics, vol. 12, 1993, pp. 1467–1470.
Noyori, R., et al., "Asymmetric Hydrogenation of β–keto Carboxylic Esters. A Practical, Purely Chemical Access to β–Hydroxy Esters in High Enantiomeric Purity", J. Am. Chem. Soc., vol. 109, 1987, pp. 5856–5858.
Ohta, T., et al., "Asymmetric Hydrogenation of Unsaturated Carboxylic Acids Catalyzed by BINAP–Ruthenium(II) Complexes", J. Org. Chem., vol. 52, 1987, pp. 3174–3176.
Ohta, T., et al., "BINAP–Ruthenium(II) Dicarboxylate Complexes: New, Highly Efficient Catalysts for Asymmetric Hydrogenations", Inorg. Chem., vol. 27, 1988, pp. 566–569.
Powell, J., et al., "Transition Metal–Carbon Bonds. Part XII. Allylic Complexes of Ruthenium(II)", J. Chem. Soc. (A), Inorg. Phys. Theor., 1968, pp. 159–161.
CAPLUS Abstract of Journal Article by Ager, David et al., Chem. Ind. (Dekker), 1995, vol. 62 (Catalysis of Organic Reactions).
CAPLUS Abstract of Journal Article by Chan et al., ACS. Symp. Sen., 1993, vol. 517 (Selectivity in Catalysis).
CAPLUS Abstract of JP 10059992, 1998.
CAPLUS Abstract of EP 366390, 1990.
CAPLUS Abstract of JP 62185044, 1987.
CAPLUS Abstract of EP 135392, 1985.
Abstract of JP 55015458, 1980, obtained from EP.ESPACENET.COM.

* cited by examiner

*Primary Examiner*—Gary Geist
*Assistant Examiner*—Leigh C. Maier
(74) *Attorney, Agent, or Firm*—Philip M. Pippenger

(57) ABSTRACT

It has been discovered that it is possible to produce enantioselectively, a chiral 2-haloalkanoic acid or salt thereof, by subjecting a 2-halo-α,β-alkenoic acid or salt, e.g., a 2-haloacrylic acid or salt, to asymmetric hydrogenation in the presence of an enantiometrically-enriched (BINAP)Ru(II) catalyst. In contrast to asymmetric hydrogenation of olefinic compounds having an electron rich, electropositive substituent in the 2-position, the substituent in the 2-position is an electronegative, electron-withdrawing halide substituent. The reaction is accelerated by inclusion of an alkali metal halide or quaternary ammonium halide in the reaction mixture.

36 Claims, No Drawings

PRODUCTION OF CHIRAL NON-RACEMIC 2-HALOPROPIONIC ACID OR SALT THEREOF

This invention relates, inter alia, to the discovery that it is possible to produce enantioselectively a chiral 2-haloalkanoic acid or salt thereof, e.g., a chiral 2-halopropionic acid or salt thereof, by subjecting a 2-halo-α,β-alkenoic acid or salt, e.g., a 2-haloacrylic acid or salt, to asymmetric hydrogenation in the presence of an enantiometrically-enriched (BINAP)Ru(II) catalyst. In contrast to asymmetric hydrogenation of olefinic compounds having an electron rich, electropositive substituent in the 2-position such as in U.S. Pat. Nos. 4,994,607; 5,198,561; and 5,202,473, the present invention involves use as the substrate reactant of a 2-haloacrylic acid or salt thereof wherein the substituent in the 2-position is an electronegative, electron-withdrawing halide substituent.

It is fortuitous that pursuant to this invention a 2-halo-α,β-alkenoic acid or salt such as a 2-haloacrylic acid or salt can be converted to a non-racemic 2-halopropionic acid in good yield and with high enantiomeric selectivity. Enantiometrically-enriched 2-haloalkanoic acids or their salts such as 2-halopropionic acids or their salts are useful as intermediates in the synthesis of aryloxyalkanoic acid herbicides having chiral carbon centers, and the need is growing for herbicidal formulations based on non-racemic rather than racemic acids. This in turn has created a need for effective and efficient process technology for producing enantiomerically-enriched 2-haloalkanoic acid intermediates that can be used in producing the desired enantiomerically-enriched aryloxyalkanoic acid herbicidal compounds. Thus the present invention can fulfill these needs most expeditiously.

In accordance with one of its embodiments, this invention provides a process wherein at least one 2-halo-α,β-alkenoic acid or salt thereof is subjected to asymmetric hydrogenation in the presence of a catalyst formed by the inclusion in the reaction mixture of at least one enantiomerically-enriched (BINAP)Ru(II) catalyst, such that at least one chiral 2-haloalkanoic acid or salt thereof is enantioselectively produced. In preferred embodiments the 2-halo-α,β-alkenoic acid or salt used is at least one 2-chloro-α,β-alkenoic acid or salt, or at least one 2-bromo-α,β-alkenoic acid or salt. Of the 2-halo-α,β-alkenoic acids or salts thereof, 2-chloroacrylic acid, 2-bromoacrylic acid, 2-chlorocrotonic acid, 2-bromocrotonic acid, or salts of these acids are particularly preferred. Most preferred is 2-chloroacrylic acid.

Another preferred embodiment involves the discovery that certain halide salts are able to accelerate the rate of the foregoing reactions in which the corresponding chiral 2-haloalkanoic acids or salts thereof are enantioselectively produced. Among suitable halide salts are alkali metal halides, ammonium halides, and quaternary ammonium halides in which the halogen atom has an atomic number greater than 9. Thus pursuant to this embodiment there is provided a process wherein at least one 2-halo-α,β-alkenoic acid or salt thereof is subjected to asymmetric hydrogenation in the presence of a catalytic system formed by the inclusion in the reaction mixture of at least one enantiomerically-enriched (BINAP)Ru(II) catalyst and at least one alkali metal halide in which the halogen atom is a chlorine, bromine or iodine atom, or at least one ammonium halide, or quaternary ammonium halide in which the halogen atom is a chlorine, bromine or iodine atom, such that at least one chiral 2-haloalkanoic acid or salt thereof is enantioselectively produced.

It is to be clearly understood that in the practice of this invention a single 2-halo-α,β-alkenoic acid or salt thereof or a mixture of a single 2-halo-α,β-alkenoic acid and a single salt thereof can be used as the initial reactant. Likewise in the practice of this invention a mixture of two or more 2-halo-α,β-alkenoic acids, or a mixture of two or more 2-halo-α,β-alkenoic acid salts, or a mixture of two or more 2-halo-α,β-alkenoic acids with two or more 2-halo-α,β-alkenoic acid salts can be used as the initial reactants. Similarly a mixture of a single 2-halo-α,β-alkenoic acid with two or more 2-halo-α,β-alkenoic acid salts or a mixture of two or more 2-halo-α,β-alkenoic acids with a single 2-halo-α,β-alkenoic acid salt can be used as the initial reactants. The acid salt(s) when used can be preformed or formed in situ.

In addition, it is to be clearly understood that this invention is not to be limited in any way to any specific composition of the catalyst(s) or catalyst system(s) once the ingredient(s) thereof has/have been included in the initial reaction mixture. At least one enantiomerically-enriched (BINAP)Ru(II) catalyst is included among the components charged to the reaction vessel. It is possible that such catalyst remains completely unchanged during the reaction. On the other hand it is possible that one or more catalytic species are formed in situ before and/or during the reaction. Thus this invention is intended to cover the catalyst(s) and/or catalyst system(s) in whatever form(s) and composition(s) such catalyst(s) and/or catalyst system(s) exist(s) in the reaction mixture during the course of carrying out the asymmetric hydrogenation reaction.

Typically the hydrogenation pursuant to this invention is performed in a liquid medium comprised at least of (i) at least one alcohol, and, at least when the initial reactant(s) comprise one or more 2-halo-α,β-alkenoic acids, (ii) at least one base capable of deprotonating the 2-halo-α,β-alkenoic acid(s) to form one or more salts that is/are soluble in said medium. Other suitable co-solvents can be employed such as a halogen-containing solvent, e.g., methylene chloride, methylene bromide, chloroform, chloroethane, 1,1- and 1,2-dichloroethane. Other co-solvents may also be used including diethyl ether, tetrahydrofuran, 1,2-dimethoxyethane, acetone, water and like solvents. The role of the co-solvent, if present, is at least partially to increase the solubility of the catalyst and/or precatalyst in the reaction medium. The substrate 2-halo-α,β-alkenoic acids or salts must have sufficient solubility in the medium for the reaction to proceed but they need not be miscible, that is, a slurry of partially dissolved substrate may be used.

In accordance with this invention, at least a substantial portion of the hydrogenation is typically performed at least at one pressure in the range of about 100 to about 3000 psig, and preferably is performed at least at one pressure in the range of about 500 to about 2000 psig. Likewise, at least a substantial portion of the hydrogenation is typically performed at least at one temperature in the range of about −20 to about 100° C., and preferably is performed at least at one temperature in the range of about 0 to about 30° C. It is not critical how much of the hydrogenation reaction is performed under the foregoing temperature and pressure conditions, as long as at least most of the hydrogenation is performed under such conditions. Thus as in most chemical processes, the assertion of exact numerical values is meaningless since things do not behave that way in the real world. In short, given a guideline, anyone of ordinary skill in the art can determine what portion of the total reaction period should be conducted under these temperature and pressure conditions in order to achieve satisfactory results when using a particular set of components in the reaction mixture.

Particularly preferred embodiments of this invention involve operating the above process utilizing the materials and operating conditions set forth in Table 1.

Enantiomerically-enriched (BINAP)Ru(II) catalysts are complexes in which a chiral phosphine ligand is complexed with a divalent ruthenium cation, the phosphine ligand being a BINAP ligand, i.e., a 2,2'-bis(diarylphosphino)-1,1'-binaphthyl ligand such as an enantiomerically-enriched 2,2'-bis(diphenylphosphino)-1,1'-binaphthyl, an enantiomerically-enriched 2,2'-bis(di-p-tolylphosphino)-1,1'-binaphthyl, an enantiomerically-enriched 2,2'-bis(di-p-tert-butyl-phenylphosphino)-1,1'binaphthyl, an enantiomerically-enriched 2,2'-bis(di-p-methoxyphenylphosphino)-1,1'-binaphthyl, an enantiomerically-enriched 2,2'-bis(di-p-ethoxyphenylphosphino)-1,1'-binaphthyl, an enantiomerically-enriched 2,2'-bis(di-p-aminophenylphosphino)-1,1'-binaphthyl, an enantiomerically-enriched 2,2'-bis(di-p-dimethylaminophenylphosphino)-1,1'-binaphthyl, an enantiomerically-enriched 2,2'-bis(dicyclohexylphosphino)-1,1'-binaphthyl, an enantiomerically-enriched 2,2'-bis(diphenylphosphino)-5,5',6,6',7,7'8,8'-octahydro-1,1'-binaphthyl and like ligands. For ease of reference, the term "enantiomerically-enriched (BINAP)Ru(II) catalyst", whether used herein in the singular or plural, refers generically to all Ru(II) complexes in which at least one enantiomerically-enriched chiral 2,2'-bis(diarylphosphino)-1,1'-binaphthyl ligand is complexed with a divalent ruthenium cation.

Preferred non-racemic (BINAP)Ru(II) catalysts are the chiral (BINAP)Ru(II) dihalide catalysts, such as the (S)- or (R)-enantiomers of 2,2'-bis(diphenylphosphino)-1,1'-binaphthyl ruthenium dichloride, 2,2'-bis(diphenylphosphino)-1,1'-binaphthyl ruthenium dibromide, 2,2'-bis(diphenylphosphino)-1,1'-binaphthyl ruthenium difluoride, 2,2'-bis(diphenyl-phosphino)-1,1'-binaphthyl ruthenium diiodide, 2,2'-bis(di-p-tolylphosphino)-1,1'-binaphthyl ruthenium dichloride, 2,2'-bis(di-p-tolylphosphino)-1,1'-binaphthyl ruthenium dibromide, 2,2'-bis(di-p-tolylphosphino)-1,1'-binaphthyl ruthenium difluoride, 2,2'-bis(di-p-tolylphosphino)-1,1'-binaphthyl ruthenium diiodide, 2,2'-bis(di-p-tert-butylphenylphosphino)-1,1'-binaphthyl ruthenium dichloride, 2,2'-bis(di-p-tert-butyl-phenylphosphino)-1,1'-binaphthyl ruthenium dibromide, 2,2'-bis(di-p-tert-butyl-phenylphosphino)-1,1'-binaphthyl ruthenium difluoride, 2,2'-bis(di-p-tert-butylphenylphosphino)-1,1'-binaphthyl ruthenium diiodide, and the like. These catalysts can be in the monomeric or dimeric form of the general formula:

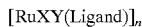

where X and Y are halogen atoms, Ligand is an enantiomerically-enriched chiral 2,2'-bis(diarylphosphino)-1,1'-binaphthyl ligand complexed with the divalent ruthenium cation, Ru, and n is 1 or 2. Similarly the catalyst may be further complexed with a tertiary amine in accordance with the general formula:

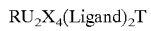

where each X is independently a halogen atom, Ligand is an enantiomerically-enriched chiral 2,2'-bis(diarylphosphino)-1,1'-binaphthyl ligand complexed with the divalent ruthenium cation, Ru, and T is a tertiary amine.

Other suitable chiral (BINAP)Ru(II) catalysts include the diacetates, the di(trifluoroacetates), the di(acetylacetonates), and the di(hexafluoroacetylacetonates). Non-limiting examples of these catalysts are 2,2'-bis(diphenylphosphino)-1,1'-binaphthylruthenium diacetate, 2,2'-bis(diphenylphosphino)-1,1'-binaphthylruthenium di(trifluoroacetate),2,2'-bis(diphenylphosphino)-1,1'-binaphthylruthenium di(acetylacetonate), and 2,2'-bis(diphenylphosphino)-1,1'-binaphthylruthenium di(hexafluoroacetylacetonate). Still other suitable chiral (BINAP)Ru(II) catalysts comprise the di(tetrafluoroborates), the di(hexafluorophosphates), the di(perchlorates), and analogous di-cationic complexes. A few examples of these catalysts are 2,2'-bis(diphenylphosphino)-1,1'-binaphthylruthenium di(tetrafluoroborate), 2,2'-bis(diphenylphosphino)-1,1'-binaphthylruthenium di(hexafluorophosphate),2,2'-bis(diphenylphosphino)-1,1'-binaphthylruthenium di(perchlorate), and like complexes.

The chiral (BINAP)Ru(II) catalysts are used in catalytic quantities. Suitable catalytic quantities typically involve proportions in the range of about 0.00002 to about 0.01 and preferably in the range of about 0.00005 to about 0.00025 mole of non-racemic (BINAP)Ru(II) catalyst(s) per mole of 2-halo-α,β-alkenoic acid(s) employed.

In a preferred embodiment, a 2-haloacrylic acid is subjected to asymmetric hydrogenation in the presence of an enantiomerically-enriched chiral (BINAP)Ru(II) catalyst, in a liquid medium comprised at least of a liquid alcohol and with which is mixed an organic base, an alkali metal base, or ammonia in order to form a salt in-situ. The organic base is preferably at least one amine, such that a chiral non-racemic 2-halopropionic acid or salt thereof is enantioselectively produced. The amine component is preferably a primary, secondary, or tertiary alkyl amine in which each alkyl group contains up to about 4 carbon atoms, such as trimethylamine, triethylamine, tripropylamine, triisopropylamine, tributylamine, tri-sec-butylamine, triisobutylamine, dimethylethylamine, diisopropylethylamine, dipropylethylamine, dimethylamine, diethylamine, diisopropylamine, dipropylamine, dibutylamine, diisobutylamine, di-sec-butylamine, methylamine, ethylamine, propylamine, isopropylamine, butylamine, isobutylamine, or sec-butylamine. The alkali metal base is preferably at least one alkali metal hydroxide, oxide, and/or alkoxide, such that a chiral 2-halopropionic acid or salt thereof is enantioselectively produced. The alkali metal component used in forming this reaction mixture is preferably lithium hydroxide, sodium hydroxide, potassium hydroxide, lithium methoxide, lithium ethoxide, lithium propoxide, lithium isopropoxide, lithium butoxide, lithium isobutoxide, sodium methoxide, sodium ethoxide, sodium propoxide, sodium isopropoxide, sodium butoxide, sodium isobutoxide, potassium methoxide, potassium ethoxide, potassium propoxide, potassium isopropoxide, potassium butoxide, potassium isobutoxide, and analogous alkali metal compounds that are soluble in the liquid reaction medium employed. Mixtures of two or more such compounds can be used, if desired. The sodium compounds are preferred, especially, sodium hydroxide, and sodium methoxide. The alkali metal base may be produced in situ, e.g. by adding an alkali metal hydride or oxide to a suitable amount of alcohol or aqueous alcohol to form the alcoxide or hydroxide, or by carefully adding lithium, sodium or potassium to the alcohol to form the alkoxide, etc. All such procedures are included within the scope of the "mixing" of the alkali metal base and the alcohol. Typically the alkali metal base will be employed in an amount in the range of about 0.5 to about 1.2 moles per mole of 2-haloacrylic acid and preferably in an amount in the range of about 0.9 to about 1.1 moles per mole of 2-haloacrylic acid.

The alcohol used is typically a liquid alcohol devoid of non-aromatic unsaturation. For example the alcohol can be a liquid alkanol such as methanol, ethanol, 1-propanol, 2-propanol, 1-butanol, 2-methyl-1-propanol, 1-methyl-1-propanol, and each of their liquid higher homologs. Likewise, alkoxyalkanols such as 2-methoxyethanol and 3-methoxypropanol can also be used. Other suitable liquid alcohols include alcohols devoid of non-aromatic unsaturation that contain a cyclic group. Examples of these include cyclopropylmethanol, cyclobutanol, cyclopentanol, cis-2-methylcyclohexanol, tetrahydrofurfuryl alcohol, benzyl alcohol, phenethyl alcohol, and similar liquid alcohols. Liquid mixtures of two or more of the foregoing types of alcohols can be used. Of the foregoing alcohols, the liquid alkanols having up to about 10 carbon atoms per molecule are preferred, with those having up to about 6 carbon atoms per molecule being more preferred. Methanol is most preferred.

It is possible, pursuant to this invention, to conduct the hydrogenation in one or a mixture of liquid alcohols containing non-aromatic unsaturation provided the corresponding saturated alcohol is also a liquid. One non-limiting illustrative example out of the vast number of such unsaturated alcohols is allyl alcohol. Numerous other such alcohols can be found in the literature. However, since some of the hydrogen would be consumed in hydrogenating the solvent, the use of such unsaturated alcohols is less preferable than using a liquid alcohol devoid of non-aromatic unsaturation. Nevertheless, the use of liquid alcohols having non-aromatic unsaturation is within the scope of this invention.

Particularly preferred embodiments of this invention involve use of the components and operating conditions set forth in Table 1.

In the embodiments of this invention wherein a rate enhancing amount of an alkali metal halide, ammonium halide, or a quaternary ammonium halide, or any mixture thereof is included in the reaction mixture, any of a variety of such halide salts can be used. As noted above, the halide anion of the salt is derived from a halogen atom having an atomic number greater than 9, i.e., the salt is an iodide, bromide, or chloride. The cation is any alkali metal, preferably Li, Na, or K, or a mixture of any two or all three of these, or is any ammonium cation such as tetralkylammonium, tetraarylammonium, trialkylammonium, triarylammonium, dialkylammonium, diarylammonium, alkylammonium, arylammonium, ammonium, or a mixture of any two or more of these, such as, for example, a mixture of two or more different tetralkylammonium halides, a mixture of two or more different tetrarylammonium halides, or a mixture of one or more tetralkylammonium halides with one or more tetrarylammonium halides. Preferred quaternary ammonium salts are tetralkylammonium halides having a total of up to about 16 carbon atoms in the molecule. As regards the halide content of the salts, preferred are the alkali metal bromides and quaternary ammonium bromides as these tend to give greater reaction acceleration than the corresponding chlorides. The most preferred salts are the alkali metal iodides and the quaternary ammonium iodides as they tend to give the greatest reaction acceleration.

The alkali metal halide, ammonium halide, or quaternary ammonium halide compounds, when used, are used in an amount sufficient to increase the reaction rate as compared to an identical reaction performed in the same way under the same conditions but in the absence of any alkali metal halide, ammonium halide, or quaternary ammonium halide. Typically this amount will fall in the range of about 3 to about 200 moles of the alkali metal halide, ammonium halide, and/or quaternary ammonium halide per mole of ruthenium catalyst being used.

In conducting the process of this invention, it is important to utilize a reactor and associated apparatus that does not contain internal residues of prior usage that would interfere with or reduce the efficiency of the hydrogenation process. Thus, in any case where the reactor is not scrupulously clean and passivated, it is desirable to suitably clean and passivate the internal surfaces that can come in contact with any portion of the reaction mixture. A preferred treatment is to soak the reactor and metal parts in a dilute hydrocarbon solution of triethylaluminum for one or more hours, then add a dilute hydrocarbon solution of a lead(II) soap, e.g., lead(II) ethylhexanoate, where upon lead metal precipitates. After cleaning with a hydrocarbon solvent and wiping out all precipitate, active sites are passivated.

Thus even if the reactor is not known to contain residues that would be harmful to the asymmetric hydrogenation, it is preferable to subject the internal surfaces of the reactor and associated apparatus (e.g., stirrer shaft and blades, internal baffles if any, internal cooling coils if any, etc.), to such pretreatment prior to use in a hydrogenation conducted pursuant to this invention.

This invention is further illustrated by the following examples. These examples are presented for illustrative purposes and are not intended to limit, and should not be construed to limit, the scope of this invention.

TABLE 1

| Entry | 2-Haloalkenoic Acid ("2-HAA") | Catalyst (2-HAA:Catalyst Mole Ratio) | Solvent | Co-solvent | Base (2-HAA:Base Mole Ratio) | Additive (Additive:Catalyst Mole Ratio) | $H_2$ Pressure, psig | Temp. °C. | Time, hours |
|---|---|---|---|---|---|---|---|---|---|
| 1 | 2-Bromoacrylic Acid | A (300–8000) | $CH_3OH$ | $CH_2Cl_2$ | $Et_3N$ (1:1) | | 4–60 | 0–25 | 24 |
| 2 | 2-Chloroacrylic Acid | B (4000–10,000) | $CH_3OH$ | $CH_2Cl_2$ | $Et_3N$ (1:1) | | 1000–2000 | 0–25 | 24 |
| 3 | 2-Chloroacrylic Acid | B (4000–10,000) | $CH_3OH$ | | $Et_3N$ (1:1) | $R_4NI$ or NaI (50–500) | 1000–2000 | 0–25 | 5–25 |
| 4 | 2-Chloroacrylic Acid | B (4000–10,000) | $CH_3OH$ | | $NaOCH_3$ (1:1) | | 1000–2000 | 0–25 | 24 |
| 5 | 2-Chloroacrylic Acid | B (4000–10,000) | $CH_3OH$ | $CH_2Cl_2$ | 50% Aq. NaOH (1:1) | NaI (10–100) | 1000–2000 | 0–25 | 5–24 |
| 6 | 2-Chloroacrylic acid | B (4000–10,000) | $CH_3OH$ | | 50% Aq. NaOH (1:1) | | 1000–2000 | 0–25 | 24 |

EXAMPLES 1–47

A number of hydrogenations pursuant to this invention were carried out and the operating conditions and results are summarized in Table 2. In these hydrogenations the reaction conditions, unless otherwise noted, involved use of:
a) 4.5 millimoles of 2-chloroacrylic acid;
b) 0.015 millimole of ruthenium as (S)-2,2'-bis(diphenylphosphino)-1,1-binaphthyl ruthenium dichloride dimer, [(S)-(BINAP)RuCl$_2$]$_2$, ("Catalyst A");
c) 9 milliliters of methanol ("MeOH"); and
d) 5 milliliters of methylene chloride ("MeCl$_2$").

The reactions were performed in a Parr stainless steel autoclave equipped with a glass liner. The reaction mixtures were stirred at 300 rpm. Decane was employed as an internal standard.

In Table 2, "MEHQ" stands for the monomethylether of hydroquinone; "Ligand A" is (S)-2,2'-bis(diphenylphosphino)-1,1'-binaphthyl; "Catalyst B" is (R)-2,2'-bis(di-p-tolylphosphino)-1,1'-binaphthyl ruthenium dichloride, (R)-Tol-BINAPRuCl$_2$; and "Catalyst C" is (R)-2,2'-bis(diphenylphosphino)-1,1'-binaphthyl ruthenium diacetate. Also in Table 2, Examples designated as A and B represent single runs carried out under the conditions specified wherein a sample of the reaction mass was taken after the specified number of hours for part A of the Example. Part B represents the completion of the reaction for the total designated period of time shown in part B of the Example.

TABLE 2

| Ex. No. | Molar Ratio[1] | Et$_3$N Equiv.[2] | Temp., °C. | H$_2$, psi | Hours | Product Yield, % | % e.e. | Comments |
| --- | --- | --- | --- | --- | --- | --- | --- | --- |
| 1 | 300 | 1.5 | 22 | 1,000 | 3 | — | 82.4 (R) | |
| 2 | 300 | 1.5 | 22 | 900 | 3 | 90 | 80.6 (R) | |
| 3 | 300 | 1.5 | 4 | 1,000 | 5.5 | 97 | 87.6 (R) | |
| 4 | 300 | 1.5 | 22 | 1,000 | 4 | 98 | 83.6 (R) | |
| 5 | 300 | 1 | 22 | 1,000 | 3 | 97 | 82.4 (R) | |
| 6 | 300 | 1 | 22 | 1,000 | 3 | 98 | 84.1 (R) | 430 ppm MEHQ added |
| 7 | 300 | 0.5 | 22 | 1,000 | 3 | 96 | 82.2 (R) | 215 ppm MEHQ added |
| 8 | 300 | 0 | 22 | 1,000 | 3 | 102 | 71.5 (R) | |
| 9 | 300 | none | 22 | 1,000 | 3.3 | 99 | 86.7 (R) | 1 equivalent of Et(iPr)$_2$N & 215 ppm MEHQ added |
| 10 | 300 | 1 | 22 | 700 | 3 | 98 | 77.2 (R) | |
| 11 | 300 | 1 | 22 | 1,000 | 3 | 95 | 68.9 (S) | Cat C & MeOH used:no co-solvent |
| 12 | 300 | 1 | 22 | 1,000 | 3 | 99 | 80.0 (S) | Cat C used |
| 13[3] | 900 | 1 | 22 | 1,000 | 3 | 98 | 82.2 (R) | |
| 14A[4] | 2,000 | 1 | 22 | 1,000 | 3 | 37 | 83.5 (R) | |
| 14B[4] | 3,000 | 1 | 22 | 1,000 | 21 | 98 | 81.4 (R) | |
| 15A[5] | 3,000 | 1 | 22 | 1,000 | 3.3 | 52 | 81.6 (R) | |
| 15B[5] | 3,000 | 1 | 22 | 1,000 | 22 | 91 | 80.8 (R) | |
| 16A[6] | 4,000 | 1 | 22 | 1,000 | 3 | 19 | 83.7 (R) | |
| 16B[6] | 4,000 | 1 | 22 | 1,000 | 23 | 99 | 81.9 (R) | |
| 17[3] | 900 | 1 | 22 | 1,000 | 3 | 97 | 81.4 (R) | Glass liner omitted |
| 18A[7] | 5,000 | 1 | 22 | 1,000 | 3 | 18 | 79.4 (R) | |
| 18B[7] | 5,000 | 1 | 22 | 1,000 | 24 | 92 | 77.4 (R) | |
| 19A[6] | 4,000 | 1 | 22 | 1,000 | 3 | 31 | 82.5 (R) | 215 ppm MEHQ added |
| 19B[6] | 4,000 | 1 | 22 | 1,000 | 20 | 95 | 81.4 (R) | |
| 20A[6] | 4,000 | 1 | 22 | 1,000 | 3 | 26 | 84.4 (R) | 1 equivalent of Ligand A relative to 2-haloacrylic acid was added |
| 20B[6] | 4,000 | 1 | 22 | 1,000 | 22 | 95 | 83.4 (R) | |
| 21 | 300 | 1 | 29 | 2,000 | 3 | 97 | 88.0 (R) | |
| 22A[6] | 4,000 | 1 | 22 | 1,000 | 3 | 23 | 81.1 (R) | |
| 22B[6] | 4,000 | 1 | 22 | 1,000 | 20 | 93 | 80.5 (R) | |
| 23 | 300 | 1 | 3 | 2,000 | 7 | 98 | 92.9 (R) | |
| 24A[6] | 4,000 | 1 | 22 | 1,000 | 3 | 17 | 82.7 (R) | 215 ppm MEHQ added |
| 24B[6] | 4,000 | 1 | 22 | 1,000 | 24 | 99 | 82.4 (R) | |
| 25 | 300 | 1 | 4 | 1,500 | 7 | 97 | 90.9 (R) | |
| 26A | 4,000 | 1 | 22 | 1,000 | 3 | 13 | 80.7 (R) | 1 equivalent of Ligand A relative to 2-haloacrylic acid was added |
| 26B | 4,000 | 1 | 22 | 1,000 | 24 | 85 | 82.0 (R) | |
| 27 | 300 | 1 | 22 | 1,000 | 3 | 45 | 98.0 (R) | 2-Bromoacrylic acid used instead of 2-chloroacrylic acid |
| 28 | 300 | none | 22 | 1,000 | 3 | 110 | 80.8 (R) | 2-Chloroacrylic acid ammonium salt used |
| 29 | 300 | 1 | 51 | 1,000 | 3 | 95 | 91.7 (R) | 2-Bromoacrylic acid used instead of 2-chloroacrylic acid |
| 30 | 300 | 1 | 22 | 1,000 | 3 | 108 | 87.8 (S) | Catalyst B used instead of Catalyst A |
| 31A | 4,000 | 1 | 22 | 1,000 | 3 | 41 | 89.5 (S) | Catalyst B used instead of Catalyst A |
| 31B | 4,000 | 1 | 22 | 1,000 | 24 | 95 | 89.0 (S) | |
| 32 | 4,000 | 1 | 22 | 1,000 | 17 | 95 | 88.7 (S) | Catalyst B used instead of Catalyst A |
| 33A | 5,000 | 1 | 22 | 1,000 | 3 | 32 | 89.2 (S) | Catalyst B used instead of Catalyst B |
| 33B | 5,000 | 1 | 22 | 1,000 | 24 | 97 | 89.3 (S) | |
| 34 | 300 | none | 22 | 1,000 | 3 | 95 | 84.8 (S) | Catalyst B used instead of Catalyst A; 1 equiv of NaH added |
| 35A | 4,000 | none | 22 | 1,000 | 3 | 26 | 77.2 (S) | Catalyst B used instead of Catalyst A; 1 equiv of NaH added; MeOH only, no co-solvent |
| 35B | 4,000 | none | 22 | 1,000 | 20 | 100 | 84.1 (S) | |
| 36A | 4,000 | none | 22 | 1,000 | 3 | 73 | 84.7 (S) | Catalyst B used instead of Catalyst A; 1 equiv of NaOH added; MeOH only, no co-solvent |
| 36B | 4,000 | none | 22 | 1,000 | 22 | 100 | 85.3 (S) | |
| 37A | 4,000 | none | 22 | 1,000 | 3 | 81 | 89.1 (S) | Catalyst B used instead of Catalyst A; 1 equiv of NaH added |
| 37B | 4,000 | none | 22 | 1,000 | 20 | 91 | 89.9 (S) | |

TABLE 2-continued

| Ex. No. | Molar Ratio[1] | Et₃N Equiv.[2] | Temp., °C. | H₂, psi | Hours | Product Yield, % | % e.e. | Comments |
|---|---|---|---|---|---|---|---|---|
| 38A | 4,000 | none | 22 | 1,000 | 3 | 61 | 86.3 (S) | Catalyst B used instead of Catalyst A; 1 equiv of NaOH & 0.24 mL of water added; MeOH only, no co-solvent |
| 38B | 4,000 | none | 22 | 1,000 | 22 | 100 | 86.5 (S) | |
| 39A | 8,000 | none | 22 | 1,000 | 24 | 82 | 84.7 (S) | Catalyst B used instead of Catalyst A; 1 equiv of NaH added; MeOH only, no co-solvent |
| 39B | 8,000 | none | 22 | 1,000 | 73 | 100 | 84.7 (S) | |
| 40A | 4,000 | none | 22 | 1,000 | 3 | 37 | 90.1 (S) | Catalyst B used instead of Catalyst A; 1 equiv of NaH added; 2.5 mL of MeCl₂ used |
| 40B | 4,000 | none | 22 | 1,000 | 22 | 100 | 89.6 (S) | |
| 41 | 8,000 | none | 22 | 1,000 | 24 | 37 | 90.1 (S) | Catalyst B used instead of Catalyst A; 1 equiv of NaOCH₃ added; 5.0 mL of MeCl₂ used |
| 42A | 4,000 | none | 22 | 1,000 | 3 | 61 | 92.2 (S) | Catalyst B used instead of Catalyst A; 1 equiv of NaOH (50% aq.) added; 5.0 mL of MeCl₂ used |
| 42B | 4,000 | none | 22 | 1,000 | 24 | 92 | 91.8 (S) | |
| 43 | 10,000 | none | 22 | 1,000 | 24 | 92 | 90.7 (S) | Catalyst B used instead of Catalyst A; 1 equiv of NaOH (50% aq.) added; 5.0 mL of MeCl₂ used |
| 44 | 4,000 | 1 | 22 | 1,000 | 3 | 93 | 85.3 (S) | Catalyst B used instead of Catalyst A; 518 equiv of Et₄NI added |
| 45A | 4,000 | 1 | 22 | 1,000 | 3 | 55 | 89.5 (S) | Catalyst B used instead of Catalyst A; 3 equiv of Et₄NI added |
| 45B | 4,000 | 1 | 22 | 1,000 | 22 | 92 | 89.7 (S) | |
| 46A | 10,000 | none | 22 | 1,000 | 3 | 20 | 91.9 | Catalyst B used instead of Catalyst A; 10 equiv of NaI added |
| 47 | 10,000 | none | 22 | 1,000 | 24 | 95 | 90.9 | |
| 47 | 10,000 | none | 22 | 1,000 | 3 | 75 | 86.2 (S) | Catalyst B used instead of Catalsyt A; 1 equiv of NaOH (50% aq.) And 1 mL of MeCl2 added |

[1]Moles of the 2-haloacrylic acid or salt thereof per mole of the ruthenium catalyst
[2]Equivalents of triethylamine relative to the 2-haloacrylic acid
[3]The amount of catalyst used was changed to 0.005 millimole
[4]The amount of catalyst used was changed to 0.00225 millimole
[5]The amount of catalyst used was changed to 0.0015 millimole
[6]The amount of catalyst used was changed to 0.001125 millimole
[7]The amount of catalyst used was changed to 0.00090 millimole The liquid reaction medium used in the process of this invention can be composed of or contain other solvent(s) and/or co-solvent(s), provided no substantial reduction in product yield or in enantiomeric excess (e.e.) is experienced as compared to use of a solvent or solvent mixture of proven efficacy, such as methanol alone or in combination with methylene chloride. Experiments have indicated, for example, that a 9:5 weight ratio of methanol:acetonitrile is a much poorer solvent system than methanol by itself as the solvent. Likewise use of tetrahydrofuran as the sole solvent gave very poor results. Therefore, it is recommended that any solvent system of unknown efficacy in the hydrogenation process of this invention be subjected to at least one preliminary pilot test to determine its suitability in the practice of this invention. If the solvent system significantly reduces the efficacy of the process, it should not be used. By "significant" or "significantly" in connection with reduction in efficacy or performance of the process is meant any situation wherein one of ordinary skill in the art would conclude from comparing the results of using a prospective solvent system against the results from use of a solvent system of known satisfactory efficacy that the prospective solvent system is sufficiently inferior in performance so that it would be undesirable to utilize the prospective solvent system in place of the solvent system of known satisfactory efficacy. Here again, in the real world a numerical value for such reduction in efficacy or performance would not be meaningful, as it would not apply in all cases. In short, adjectives such as "substantial" and "significant" and their corresponding adverbial forms should always be interpreted with the use of common sense. Oftentimes such words are the most precise way of expressing information.

EXAMPLES 48–54

The surprising rate accelerating effect of alkali metal halides and of quaternary ammonium halides when used in combination with one or more enantiometrically-enriched (BINAP)Ru(II) catalysts was demonstrated in another series of experiments summarized in Table 3. In these experiments the effect on the initial reaction rate was determined by stopping the reactions, conducted under otherwise identical conditions but with varying amounts and identities of halide salts, after three hours at 22° C. and 1000 psig of hydrogen. Analysis by NMR allows calculation of the average catalyst turnover (TO) frequency, expressed as TO/h, for each reaction. The turnovers are defined as moles of product formed per mole of ruthenium catalyst. Parallel analysis by GC allowed determination of enantiomeric excess ("% e.e."). The reaction conditions used were as follows: 2-chloroacrylic acid ("2-CAA"), 9.00 mmol; 2,2'-bis(di-p-tolylphosphino)-1,1'-binaphthyl ruthenium dichloride ("TolBinapRuCl₂"), 0.900 mL of a 1.00 mM solution in CH₂Cl₂; NaOH, 0.475 mL of a 18.9 M degassed aqueous solution; CH₂Cl₂, 4.10 mL; decane internal standard, 0.220 mL; CH₃OH, 7–9 mL to maintain a volume of 16 mL. Hydrogen pressure was 1000 psig. Reaction temperature was 22° C. using a stirring rate of 300 rpm. Reaction time was 3.0 hours.

It will be seen from Table 3 that increasing amounts of iodide increase the reaction rate to a limit reached at about 0.090 mM iodide concentration, 100 equivalents with respect to ruthenium in these reactions. Further increases in iodide concentration did not increase the rate. Reactions with chloride and bromide salts also increased the reaction rate but to a lesser degree, the order of effectiveness being I>Br>Cl.

TABLE 3

| Example | Additive*, mM | % 2-CAA Recovered | % 2-CPA Yield | % e.e. | TO/h |
|---------|---------------|-------------------|---------------|--------|------|
| 48 | — | 87.4 | 12.6 | 92 | 420 |
| 49 | NaI, 0.023 | 76.4 | 20.6 | 92 | 687 |
| 50 | NaI, 0.045 | 78.5 | 22 | 92 | 733 |
| 51 | NaI, 0.090 | 63.2 | 36.8 | 92 | 1,230 |
| 52 | NaI, 0.180 | 63.1 | 36.9 | 92 | 1,230 |
| 53 | Bu$_4$NBr, 0.180 | 72.5 | 27.5 | 92 | 916 |
| 54 | Bu$_4$NCl, 0.180 | 77.5 | 22.5 | 91 | 733 |

*NaI added as a methanolic stock solution; others added as solids with MeOH makeup.

Compounds referred to by chemical name or formula anywhere in this document, whether referred to in the singular or plural, are identified as they exist prior to coming into contact with another substance referred to by chemical name or chemical type (e.g. another component, a solvent, or etc.). It matters not what preliminary chemical changes, if any, take place in the resulting mixture or solution, as such changes are the natural result of bringing the specified substances together under the conditions called for pursuant to this disclosure. Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises subjecting at least one 2-halo-α,β-alkenoic acid and/or salt thereof, to asymmetric hydrogenation in a liquid phase reaction mixture and in the presence of a catalytic system formed by the inclusion in the reaction mixture of (a) at least one enantiomerically-enriched (BINAP)Ru(II) catalyst and (b) at least one alkali metal halide, ammonium halide, or quaternary ammonium halide in which the halide is derived from a halogen atom of atomic number greater than 9, such that at least one chiral 2-haloalkanoic acid and/or salt thereof is enantioselectively produced.

2. A process of claim 1 wherein said catalyst in the form immediately prior to being included as a component of the reaction mixture is an enantiometrically-enriched (BINAP) Ru(II) dihalide catalyst.

3. A process of claim 1 wherein said catalyst in the form immediately prior to being included as a component of the reaction mixture is an enantiometrically-enriched (BINAP) Ru(II) dichloride catalyst.

4. A process of claim 3 wherein said catalyst in the form immediately prior to being included as a component of the reaction mixture is enantiometrically-enriched 2,2'-bis (diphenylphosphino)-1,1'-binaphthyl ruthenium dichloride dimer.

5. A process of claim 3 wherein said catalyst in the form immediately prior to being included as a component of the reaction mixture is enantiometrically-enriched 2,2'-bis(di-p-tolylphosphino)-1,1'-binaphthyl ruthenium dichloride.

6. A process of any of claims 1–5 wherein said hydrogenation is performed in a liquid medium comprised of (i) an alcohol, (ii) a halogen-containing co-solvent, and (iii) at least when at least one 2-halo-α,β-alkenoic acid is employed, at least one base capable of deprotonating the 2-halo-α,β-alkenoic acid(s) to form at least one salt that is soluble in said medium.

7. A process of any of claims 1–5 wherein said hydrogenation is performed in a liquid medium comprised of (i) an alcohol, (ii) a co-solvent, and (iii) a base capable of deprotonating the 2-halo-α,β-alkenoic acid(s) to form at least one salt that is soluble in said medium.

8. A process of any of claims 1–5 wherein at least most of said hydrogenation is performed at least at one pressure in the range of about 100 to about 3000 psig, and at least at one temperature in the range of about −20 to about 100° C.

9. A process of claim 1 wherein said at least one 2-halo-α,β-alkenoic acid and/or salt thereof is at least one 2-haloacrylic acid and/or salt thereof.

10. A process of claim 9 wherein said catalyst in the form immediately prior to being included as a component of the reaction mixture is an enantiometrically-enriched (BINAP) Ru(II) dihalide catalyst.

11. A process of claim 9 wherein said catalyst in the form immediately prior to being included as a component of the reaction mixture is an enantiometrically-enriched (BINAP) Ru(II) dichloride catalyst.

12. A process of claim 11 wherein said catalyst in the form immediately prior to being included as a component of the reaction mixture is enantiometrically-enriched 2,2'-bis (diphenylphosphino)-1,1'-binaphthyl ruthenium dichloride dimer.

13. A process of claim 11 wherein said catalyst in the form immediately prior to being included as a component of the reaction mixture is enantiometrically-enriched 2,2'-bis(di-p-tolylphosphino)-1,1'-binaphthyl ruthenium dichloride.

14. A process of any of claims 9–13 wherein said hydrogenation is performed in a liquid medium comprised of (i) an alcohol, (ii) a co-solvent, and (iii) a base capable of deprotonating 2-haloacrylic acid to form a salt that is soluble in said medium.

15. A process of claim 14 wherein said co-solvent is a halogen-containing co-solvent.

16. A process of any of claims 9–13 wherein at least most of said hydrogenation is performed at least at one pressure in the range of about 100 to about 3000 psig.

17. A process of any of claims 9–13 wherein said 2-haloacrylic acid is 2-chloroacrylic acid; wherein said hydrogenation is performed in a liquid medium comprised of (i) an alcohol, (ii) a halogen-containing co-solvent, and (iii) a base capable of deprotonating 2-chloroacrylic acid to form a salt that is soluble in said medium; and wherein at least a substantial portion of said hydrogenation is performed at least at one pressure in the range of about 100 to about 3000 psig, and at least at one temperature in the range of about −20 to about 100° C.

18. A process which comprises subjecting at least one 2-haloacrylic acid and/or salt thereof, to asymmetric hydrogenation in at least one liquid alcohol reaction medium with which at least one alkali metal base is mixed, and in the presence of a catalyst that is:

1) at least one enantiomerically-enriched (BINAP)Ru(II) catalyst;
2) catalytic species, if any, formed by the inclusion of at least one enantiomerically-enriched (BINAP)Ru(II) catalyst as a component used in making up the reaction mixture; or
3) both of 1) and 2);

such that at least one enantiomerically-enriched 2-halopropionic acid and/or salt thereof is enantioselectively produced.

19. A process of claim 18 wherein the alkali metal base that is mixed with said at least one liquid alcohol is a hydride, a hydroxide, an oxide, or an alkoxide.

20. A process of claim 18 wherein the alkali metal base that is mixed with said at least one liquid alcohol is lithium, sodium, or potassium hydride, hydroxide, oxide, or alkoxide.

21. A process of claim 18 wherein the alkali metal base that is mixed with said at least one liquid alcohol is sodium hydride, sodium hydroxide, or sodium alkoxide, and wherein said at least one liquid alcohol is a liquid alcohol devoid of non-aromatic unsaturation.

22. A process of claim 18 wherein the alkali metal base that is mixed with said at least one liquid alcohol is sodium hydride, and wherein said at least one liquid alcohol is methanol.

23. A process of any of claims 18–22 wherein said catalyst in the form immediately prior to being included as a component of the reaction mixture is enantiometrically-enriched 2,2'-bis(diphenylphosphino)-1,1'-binaphthyl ruthenium dichloride or enantiometrically-enriched 2,2'-bis(p-tolylphosphino)-1,1'-binaphthyl ruthenium dichloride.

24. A process which comprises subjecting at least one 2-halo-α,β-alkenoic acid and/or salt thereof, to asymmetric hydrogenation in the presence of
   (a) a catalyst that is
      1) at least one enantiomerically-enriched (BINAP)Ru(II) catalyst;
      2) catalytic species, if any, formed by the inclusion of at least one enantiomerically-enriched (BINAP)Ru(II) catalyst as a component used in making up the reaction mixture; or
      3) both of 1) and 2); and
   (b) at least one alkali metal halide in which the halide is derived from a halogen atom of atomic number greater than 9 and/or at least one quaternary ammonium halide in which the halide is derived from a halogen atom of atomic number greater than 9;
in at least one liquid alcohol reaction medium with which at least one alkali metal base is mixed; and at a pressure in the range of about 100 to about 3000 psig and a temperature in the range of about 0 to about 30° C., such that an enantiomerically-enriched 2-haloalkanoic acid or salt thereof is enantioselectively produced.

25. A process of claim 24 wherein said at least one 2-halo-α,β-alkenoic acid and/or salt thereof is a 2-haloacrylic acid or a salt thereof or a 2-halocrotonic acid or a salt thereof.

26. A process of claim 24 wherein said at least one 2-halo-α,β-alkenoic acid and/or salt thereof is 2-chloroacrylic acid or a salt thereof.

27. A process of any of claims 24–26 wherein said catalyst in the form immediately prior to being included as a component of the reaction mixture is an enantiometrically-enriched (BINAP)Ru(II) dihalide catalyst.

28. A process of any of claims 24–26 wherein said catalyst in the form immediately prior to being included as a component of the reaction mixture is an enantiometrically-enriched (BINAP)Ru(II) dichloride catalyst.

29. A process of any of claims 24–26 wherein said catalyst in the form immediately prior to being included as a component of the reaction mixture is enantiometrically-enriched 2,2'-bis(diphenylphosphino)-1,1'-binaphthyl ruthenium dichloride dimer.

30. A process of any of claims 24–26 wherein said catalyst in the form immediately prior to being included as a component of the reaction mixture is enantiometrically-enriched 2,2'-bis(di-p-tolylphosphino)-1,1'-binaphthyl ruthenium dichloride.

31. A process of any of claims 24–26 wherein said alkali metal halide and/or quaternary ammonium halide is at least one alkali metal bromide and/or at least one quaternary ammonium bromide.

32. A process of any of claims 24–26 wherein said alkali metal halide and/or quaternary ammonium halide is at least one alkali metal iodide and/or at least one quaternary ammonium iodide.

33. A process of any of claims 24–26 wherein said catalyst in the form immediately prior to being included as a component of the reaction mixture is an enantiometrically-enriched (BINAP)Ru(II) dihalide catalyst, and wherein said alkali metal halide and/or quaternary ammonium halide is (i) an alkali metal bromide, (ii) an alkali metal iodide, (iii) a quaternary ammonium bromide, (iv) a quaternary ammonium iodide, or (v) a mixture of any two or more of (i) through (iv).

34. A process of any of claims 24–26 wherein said catalyst in the form immediately prior to being included as a component of the reaction mixture is an enantiometrically-enriched (BINAP)Ru(II) dichloride catalyst, and wherein said alkali metal halide and/or quaternary ammonium halide is (i) an alkali metal bromide, (ii) an alkali metal iodide, (iii) a quaternary ammonium bromide, (iv) a quaternary ammonium iodide, or (v) a mixture of any two or more of (i) through (iv).

35. A process of any of claims 24–26 wherein said catalyst in the form immediately prior to being included as a component of the reaction mixture is enantiometrically-enriched 2,2'-bis(diphenylphosphino)-1,1'-binaphthyl ruthenium dichloride dimer, and wherein said alkali metal halide and/or quaternary ammonium halide is (i) sodium bromide or potassium bromide, (ii) sodium iodide or potassium iodide, (iii) a tetraalkyl ammonium bromide, (iv) a tetraalkyl ammonium iodide, or (v) a mixture of any two or more of (i) through (iv).

36. A process of any of claims 24–26 wherein said catalyst in the form immediately prior to being included as a component of the reaction mixture is enantiometrically-enriched 2,2'-bis(di-p-tolylphosphino)-1,1'-binaphthyl ruthenium dichloride, and wherein said alkali metal halide and/or quaternary ammonium halide is (i) sodium bromide or potassium bromide, (ii) sodium iodide or potassium iodide, (iii) a tetraalkyl ammonium bromide, (iv) a tetraalkyl ammonium iodide, or (v) a mixture of any two or more of (i) through (iv).

* * * * *